United States Patent [19]

Brewer et al.

[11] 4,228,149
[45] Oct. 14, 1980

[54] SUSTAINED RELEASE COMPOSITIONS

[75] Inventors: Malcolm D. Brewer, Northgate Crawley; Gerald J. L. Griffin, London, both of England

[73] Assignee: Beecham Group Limited, England

[21] Appl. No.: 910,278

[22] Filed: May 30, 1978

[30] Foreign Application Priority Data

Jun. 9, 1977 [GB] United Kingdom ............... 24178/77

[51] Int. Cl.² ........................... A61K 9/20; A61K 9/24
[52] U.S. Cl. ..................................... 424/14; 128/260; 424/16; 424/19; 424/21; 424/27; 424/28; 424/32; 424/33
[58] Field of Search ................................. 424/14–28, 424/32, 33; 128/260

[56] References Cited

U.S. PATENT DOCUMENTS

| | | | |
|---|---|---|---|
| 3,625,214 | 12/1971 | Higuchi | 128/260 |
| 3,832,252 | 8/1974 | Higuchi et al. | 156/86 |
| 4,029,757 | 6/1977 | Mlodozeniec et al. | 424/27 |
| 4,029,758 | 6/1977 | Mlodozeniec et al. | 424/27 |
| 4,031,200 | 6/1977 | Reif | 424/27 |
| 4,072,551 | 2/1978 | Dabal et al. | 156/378 |

FOREIGN PATENT DOCUMENTS 2274 of 1869 United Kingdom ..................... 424/14

*Primary Examiner*—Shep K. Rose
*Attorney, Agent, or Firm*—Jacobs & Jacobs

[57] ABSTRACT

Sustained release composition comprising a water soluble veterinary medicament dispersed in a sheet of water insoluble polymer, which sheet is of a size and composition such that it is capable of being constrained in a position which allows oral administration and is, in the rumen, capable of moving relative to this position to retain the composition therein.

24 Claims, 6 Drawing Figures

SUSTAINED RELEASE COMPOSITIONS

This invention relates to a device giving sustained release of a veterinary medicament, a process for the preparation of such devices and a method for their use.

Ruminant animals, particularly cattle and sheep, form an important group of animals which require periodic administration of veterinary medicaments for the treatment and alleviation of various conditions. For example, it is often desirable to treat such animals, either therapeutically or prophylactically, with anthelmintics. The repeated administration of such veterinary medicaments to animals at frequent time intervals is expensive and inconvenient.

U.K. Pat. No. 1318259 describes a number of devices for retaining slow release veterinary medicament formulations in the rumen over an extended period of time, and therefore achieving the desired result. This prolonged retention in the rumen is obtained by the devices having a relatively narrow first configuration which allows the devices to be administered per os to the ruminant, and a relatively broad second configuration which the devices assume or are caused to assume in the rumen thereby hindering or preventing their passage out of the rumen.

A typical example of such a device specifically described in the Patent is a plastic cylindrical capsule containing a detergent for the control of bloat in cattle. The capsule is 150 mm long and 30 mm wide (thereby allowing per os administration), and consists of two half-cylinders hinged along one edge. The hinges are made from rubber and are biased so that the two half-cyclinders spring apart in the rumen and thus become too wide to pass out through the rumen or to be regurgitated through the oesophagus. Each half-cylinder contains a gel of ethyl cellulose containing the desired anti-bloat agent which is leached from the gel by the rumen fluids over an extended period of time. The hinges are constructed so that under the rumen conditions they pull away from the half-cylinders after effective release of the agent thereby facilitating regurgitation of the fragmented device.

Another example of such a device described in the Patent is a 'doughnut-shaped' ring made of an ethyl cellulose gel containing the desired anti-bloat agent. For administration the ring is deformed to an elongate configuration by means of a gelatin tape. In the rumen this tape dissolves and due to the resilience of the ring it reverts to its original configuration thereby preventing or hindering regurgitation thereof.

It has now been found that the desired sustained release of water soluble medicaments can be obtained by dispersing the medicament in a water insoluble polymer sheet which sheet has a size and composition so that it can be constrained narrow enough for administration and yet move in the rumen to a position in which it is sufficiently broad to prevent regurgitation. This is particularly surprising as nowhere in U.K. Pat. No. 1318259 is this simple, cheap, strong and easily manufactured solution to the problem in any way suggested. In fact the only relevant use for polymers revealed in the Patent is as a protective material to allow medicament incorporated therein and administered via the plastic cylindrical capsule to by-pass the rumen.

Accordingly, the present invention provides a device comprising a water soluble veterinary medicament dispersed in a sheet of water insoluble polymer, which sheet is of a size and composition such that it is capable of being constrained in a position which allows oral administration and is, in the rumen, capable of moving relative to this position to retain the device therein.

When used herein the term "water-soluble veterinary medicament" means a medicament having a solubility in water at 39° C. of not less than 0.1%, preferably 1% w/v.

When used herein the term "water-insoluble polymer" means a polymer having a solubility in water at 39° C. of not more than 0.001% w/v.

The sheet may be made from any inert polymer which is insoluble in water and which is sufficiently resilient to be capable of being constrained in a position which allows oral administration and which is, in the rumen, capable of moving relative to this constrained position to an open position. The size of the sheet must be such that in this open position it provides a sufficiently great cross-sectional area to prevent regurgitation. The skilled worker will be able by simple experiment to produce sheets having these necessary properties now that the advantageous properties thereof have been discovered.

By way of example, we have found that particularly suitable sheets can be made from ethylene-vinyl acetate copolymer. Suitably these copolymers will contain about 10 to 60% vinyl acetate.

The size and shape of the sheets will of course depend on the ruminant animals for which they are intended. By way of example, for sheep the sheet is suitably of a thickness 1 to 3 mm., a length 5 to 8 cm, and a width 3 to 5 cm. Similarly for cattle suitable dimensions are respectively 2 to 4 mm, 7 to 10 cm and 4 to 7 cm.

Provided the veterinary medicament has the required water solubility and is compatible with the polymer in which it is dispersed, any medicament maybe used.

Examples of suitable medicaments include anthelmintics such as morantel, pyrantel, tetramisole, levamisole, butamisole, nitramisole and diethyl carbamazine and salts thereof, and salts of nitroxynil such as the N-ethyl glucamine salt. Piperazine and salts thereof may also be used.

More suitably, the anthelmintic is chosen from morantel, pyrantel, tetramisole, levamisole, or a salt thereof.

Preferred examples of anthelmintics include morantel or a salt thereof, such as salts with organic acids, e.g. citrate and tartrate, and levamisole or a salt thereof such as the hydrochloride.

Other suitable medicaments include insecticides, methane inhibitors, coccidiostats, vitamins, mineral supplements (such as copper, selenium, cobalt or magnesium), growth promotors and the like.

The medicament must not represent so great a percentage of the sheet that the sheet loses its necessary resilience. Thus suitably the medicament will represent 30 to 75% by weight of the sheet, more suitably 40 to 65% by weight, for example 60% by weight.

Provided the sheet retains its essential physical properties, the quantity of medicament dispersed therein will depend on the length of time for which the sustained therapy is intended, the nature of the medicament, and the species of animal being treated. Simple experiment will enable suitable relatively quantities for any medicament polymer system to be determined. By way of example, with morantel citrate we have found that 2 to 4 g. for sheep and 5 to 10 g. for cattle is suitable.

From the aforesaid it will be realized that one particularly useful embodiment of the invention provides a device comprising a water soluble anthelmintic dispersed in a sheet of ethylene-vinyl acetate copolymer, which sheet is of a size and composition such that it is capable of being constrained in a position which allows oral administration and is, in the rumen, capable of moving relative to this position to retain the device therein.

Preferably in this device the anthelmintic is morantel or a salt thereof, or levamisole or a salt thereof.

The invention also provides a preferred device comprising a water soluble veterinary medicament dispersed in a sheet of water insoluble polymer; which sheet is coated by a film and is of a size and composition such that it is capable of being constrained in a position which allows oral administration and is, in the rumen, capable of moving relative to this position to retain the device therein; which film comprises a water-insoluble polymer.

The presence of the film coating the sheet enables the release rate of medicament from the sheet to be varied.

A water degradable filler may be included in the film to further vary the release properties of the sheet. In the rumen the degradable filler, which may for example be water soluble and/or biodegradable, gradually decomposes forming ducts and channels connecting the free surface of the film with the surface of the sheet to which it is bound. The rumen liquor can then penetrate these pores and act upon the sheet surface to leach medicament therefrom. At the same time medicament is being continually leached by the rumen liquors from uncoated portions of the sheet.

It will be apparent that the release properties of the sheet may be varied as desired by varying the percentage of the surface area of the sheet coated, the thickness of the film, and the percentage of the degradable filler in the film.

Suitably the film coats both surfaces of the sheet, and not its edges. In this manner relatively rapid instantaneous release is obtained from the edges of the sheet, and delayed relatively slow release is obtained through the coated surfaces of the sheet.

It has been found that when present the degradable filler suitably represents 20 to 60%, more suitably 30 to 50% by weight of the film. Suitable fillers for use according to the invention include compounds such as starch and lactose. Starch is a preferred filler.

Suitably the thickness of the film will be 0.1 to 0.5 mm., more suitably 0.2 to 0.4 mm.

Preferred devices of this nature have sheets and coating films made from ethylene-vinyl acetate copolymer.

Suitably the medicament in such preferred compositions is an anthelmintic such as morantel or a salt thereof.

Most preferably the device has a sheet of ethylene-vinyl acetate copolymer UE 631 containing 60% morantel citrate and of thickness 1.0 to 1.5 mm., and coating films on both surfaces of the sheet of ethylene-vinyl acetate copolymer EY 902 containing 35 to 40% starch and of thickness 0.2 to 0.4 mm.

The release properties of the devices of the invention may be further varied by forming a hole or holes in the sheets. However we have found that the best results are obtained without such holes.

The necessary constraint to the devices to allow oral administration may be applied to the device by the throat of the animal itself. However it is normally preferred that some constraining means is associated with the device to hold it in this position for administration purposes. The constraining means is chosen so that it is quickly removed in the rumen environment to allow the sheet to unfold once it is in the rumen in the manner of the invention. This constraining means may be any element that is able to hold the device in its constrained position for administration, but is readily dissolved, destroyed, ruptured or otherwise removed by the rumen environment. Examples of suitable constraining means include gelatin string, gelatin tape, paper strips backed by water soluble adhesive, and water soluble paper.

The device is suitably formed into its constrained position by folding or rolling up the sheet.

The constrained device may be coated with a water soluble plastic envelope to improve its appearance, to ease administration and to enhance the storage stability of the device. Of course if desired this coating may itself provide the necessary constraint.

The devices will suitably weigh around 5–10 g. for sheep and around 6 to 20 g. for cattle.

The invention also provides a method of treatment of disorders in ruminant animals, which method comprises the oral administration to the animal of a device according to the invention.

It has been found the devices of the invention give a sustained release of medicament in the rumen thereby reducing the number of doses necessary to effect control or prophylaxis of disease.

The invention also provides a process for the preparation of the devices of the invention, which process comprises dispersing the medicament in the polymer.

This process may often suitably be carried out by softening pre-formed polymer and blending therein the medicament. For example the process may suitably be carried out by running a strip of polymer through a roll mill, which mill is heated to a temperature sufficient to soften the polymer but not to decompose the medicament. The medicament is then steadily added to the nip of the mill, and the strip of polymer recirculated until the required composition is achieved.

The strip is then formed into a sheet of the desired dimensions, suitably by cutting. It may first, if necessary, be hot pressed to the desired thickness, for example between two polished steel plates.

The preferred compositions of the invention wherein a coating film is present may simply be prepared by heating together the sheet and the film in the desired relative position in a press. The polymer and the film may be prepared in conventional manner.

One embodiment of the invention will now be described with reference to the accompanying drawing, in which.

Figure 1:
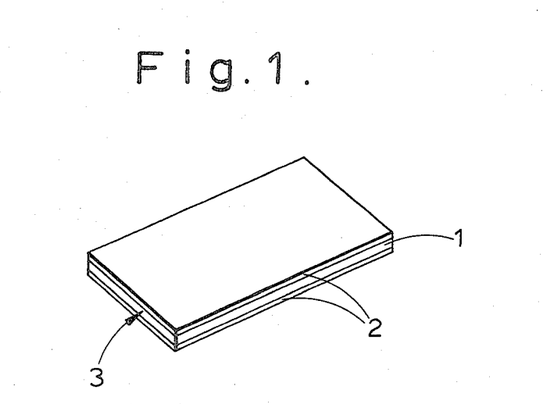
FIG. 1 is a perspective view of a device according to the invention.

The device of FIG. 1 has a sheet 1 comprising 65% morantel citrate and 35% ethylene vinyl acetate copolymer (E.V.A.) grade UE631. This sheet 1 is approximately 1 mm. thick, 4 cm wide and 6 cm long.

The sheet 1 is coated by two films 2, each of which comprises 50% lactose and 50% E.V.A. grade UE631, and is of an approximate thickness of 0.3 mm. The edge surfaces 3 of the sheet 1 are not coated by film.

Figure 2:
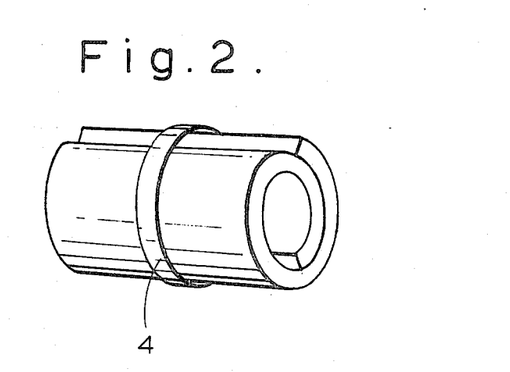
FIG. 2 is a perspective view of the device of FIG. 1 in its administration form.

FIG. 2 shows the device rolled up for administration to a sheep, and held in this configuration by a strip of paper 4 gummed with a water-soluble adhesive. After administration per os to the sheep, the paper strip unsticks under the action of the rumen liquor, and the device, due to its resilience moves into a substantially flat configuration to block regurgitation.

The following Examples illustrate further features of the invention:

EXAMPLE 1

Devices in plain sheet form

The following method was used to prepare a sheet containing 50% morantel citrate, 50% ethylene vinyl acetate copolymer (E.V.A.).

50 g. E.V.A. (grade UE 631 containing 18.21% vinyl acetate content) was fluxed on a 25×7 cm. 2-roll mill and when it was running as a smooth hide, 50 g. of morantel citrate powder was steadily added to the nip. The hide was cut and turned many times to ensure uniformity. The machine was oil heated to a temperature of 100° C. sufficient to flux the resin but not so high that the compound stuck to the rolls or the drug decomposed.

From this 100 g. mixture, 20 g. portions of the rough hide from the mill were hot-pressed into sheets 1 mm. thick, within a steel frame (internal dimensions 15.5×10.5 cm.), between polished steel plates for two minutes at a pressure of 280 kg. cm-2 and temperature of 100° C. Melinex polyester foil was used as a facing material to enable the copolymer to be released easily from the press.

Samples from these sheets were then cut.

A number of other devices were prepared in the same manner, with different proportions of morantel and polymer. The constituents of these devices are shown in the following Table 1.

Table 1

| Constituents of morantel/polymer sheets | | |
|---|---|---|
| Composition Number | Weight morantel citrate g. | Weight E.V.A. (UE 631)g. |
| 1 | 20 | 80 |
| 2 | 30 | 70 |
| 3 | 40 | 60 |
| 5 | 60 | 40 |

EXAMPLE 2

Devices comprising sheets coated with film

The following method was used to prepare a sandwich device, containing a centre core of 65% morantel citrate, 35% E.V.A. (grade UE 631) with an outer skin containing 50% lactose, 50% E.V.A. (grade UE 631).

The material for the outer skin was prepared by blending 50 g. lactose with 50 g. E.V.A. (grade UE 631) on a two-roll mill, oil heated to a temperature of 100° C., similar to the method described in Example 1.

A thin sheet (0.2-0.4 mm. thick), of this mixture was obtained by pressing 20 g. of this material between polished steel plates at a temperature of 100° C. and pressure of 280 kg cm-2 for 5 minutes. Melinex polyester film was used as a facing material.

The material for the inner core was prepared by blending 65 g morantel citrate with 35 g E.V.A. (grade UE 631) on a two-roll mill, oil heated to a temperature of 100° C., as described previously. From this mixture, 20 g portions were pressed into sheets 1 mm. thick, within a steel frame (internal dimensions 15.5×10.5 cm) between polished steel plates for two minutes at a temperature of 100° C. and pressure of 280 kg cm$^{-2}$. Melinex polyester foil was used as a facing material to enable the material to be released easily from the press.

The final sandwich was prepared by heating a sheet of centre core mixture containing 65% morantel citrate and 35% E.V.A. between two sheets of the mixture containing 50% lactose, 50% E.V.A. between polished steel plates in a press at 100° C. for two minutes. Melinex polyester foil was used as a facing material as before.

Samples for in vitro testing were cut from the centre of the pressed sandwich either by scalpel or guillotine. Further devices were prepared in the same manner as described above but with different proportions of polymer, morantel, starch and lactose. Examples are shown in the following Table 2. The size of each sample cut was 2×3 cm.

Table 2

| Constituents of alternative sandwich devices | | | | |
|---|---|---|---|---|
| Outer Skin | | | Inner Core | |
| Polymer | | Starch/Lactose | Polymer | Morantel citrate |
| UE 631 | 100g | Lactose 0g | UE 631 40g | 60g |
|  | 70g |  30g |  |  |
|  | 65g |  35g |  |  |
|  | 60g |  40g |  |  |
|  | 55g |  45g |  |  |
|  | 50g |  50g |  |  |
|  | 45g |  55g |  |  |
|  | 40g |  60g |  |  |
| UE 631 | 100g | Lactose 0g | UE 631 35g | 65g |
|  | 70g |  30g |  |  |
|  | 65g |  35g |  |  |
|  | 60g |  40g |  |  |
|  | 55g |  45g |  |  |
|  | 45g |  55g |  |  |
|  | 40g |  60g |  |  |
| UE 631 | 50g | Starch 50g | UE 631 35g | 65g |
|  | 60g |  40g |  |  |
| UE 631 | 60g | Starch 40g | UE 631 40g | 60g |
| UE 631 | 100g | NIL | EY 902 40g | 60g |
| UE 631 | 100g | NIL | EY 902 30g | 70g |
| EY 902 | 50g | Lactose 50g | UE 631 35g | 65g |
| EY 902 | 30g | Starch 70g | UE 631 35g | 65g |
|  | 40g |  60g |  |  |
|  | 50g |  50g |  |  |
|  | 60g |  40g |  |  |
|  | 70g |  30g |  |  |

Materials Used

Polymers. Ethylene vinyl acetate copolymer.

| Trade Mark | Ultrathene | Ultrathene |
|---|---|---|
| Type | UE 631 | EY 902 |
| Vinyl acetate content | 18–21% | 41.7% |
| Melt flow index | 1.8 | 4.05 |
| Density | 941 Kilos m$^{-3}$ | 967 Kilos m$^{-3}$ |
| Address of Manufactures — | U.S.I. Europe N.V. P.O. Box 529 B - 2000 Antwerp, Belgium. | |

Starch. Maize or corn starch.

Lactose. α Lactose hydrate,

Available from — Sigma Chemical Co., Kingston-on-Thames, Surrey.

EXAMPLE 3

In vitro Drug Release Test

The release of morantel from certain of the compositions prepared in Example 2 was examined in vitro.

Four samples of each composition were separately placed in screw-capped bottles containing 20 ml of phosphate buffered saline pH 6.8. 1 ml of a 1% solution of α amylase enzyme (ex. B. subtilis) was added to the compositions containing starch. In the test, the bottles were continously rotated in a drum at a temperature of 39° C. The samples were changed to fresh bottles of liquid during the first 4 days and thereafter once or twice a week. The 'morantel' released from these samples was assayed using a Beckmann U.V. Spectrophotometer at 325 nm after calibration with standard drug solutions and the starch breakdown products and lactose released were assayed on an Eel colorimeter using dinitrosalicylic acid colour reagent after calibration with standard maltose and lactose solutions. The results obtained were shown in Table 3.

The results obtained clearly shown that sustained release is achieved in all cases, and that the rate of release may be varied by alteration of the ingredients of the devices and/or their inclusion levels.

Device A—30% starch+70% E.V.A. (grade EY 902)
Device B—35% starch+65% E.V.A. (grade EY 902)
Device C—40% starch+60% E.V.A. (grade EY 902)
Device D—One outer layer as Device A; second outer layer as Device B.

Overall dimensions in the flat configuration were ca. 8×4×0.2 cm. For dosing, the sandwiches were rolled into cylinders measuring ca. 8×1.3 cm.

Thirty-two devices were made from groups A, B and D and twenty-seven for C. Individual weights of devices were in the range 7–8 g, the morantel citrate content being 3.0–3.5 g.

Morantel weights were selected so as to provide release of drug at a rate of ca. 1.6 mg/kg/day.

Animals used

72 Lambs were used for the anthelmintic test; these were divided into six groups of 12 and treated as follows:

Group 1  Untreated controls.
Group 2  Single treatments with morantel

TABLE 3

| | | Mg. morantel released in vitro from sandwich devices | | | | | | | | | | | | | | | |
|---|---|---|---|---|---|---|---|---|---|---|---|---|---|---|---|---|---|
| | | Time in days | | | | | | | | | | | | | | | |
| Outer Skin | Inner core | 1 | 2 | 3 | 4 | 7 | 10 | 14 | 17 | 21 | 24 | 28 | 35 | 42 | 49 | 56 | 63 | 70 |
| 50% lactose 50% UE 631 | 65% morantel 35% UE 631 | 51.0 | 14.6 | 15.4 | 11.4 | 34.8 | 31.35 | 31.7 | 19.6 | 21.5 | 12.5 | 18.9 | 27.6 | 11.2 | 17.1 | | | |
| 100% UE 631 | 65% morantel 35% UE 631 | 46.4 | 13.8 | 11.7 | 7.7 | 30.6 | 24.8 | 26.1 | 14.9 | 22.2 | 14.5 | 11.7 | 25.6 | 26.2 | 18.7 | | | |
| 50% starch 50% EY 902 | 65% morantel 35% UE 631 | 66.0 | 26.8 | 20.0 | 17.2 | 49.1 | 36.6 | 45.0 | 28.8 | 16.6 | 24.4 | 18.2 | 39.7 | 29.1 | 21.2 | 11.5 | 0.7 | 0.3 |
| 55% lactose 45% UE 631 | 65% morantel 35% UE 631 | 76.4 | 27.1 | 13.2 | 16.5 | 45.6 | 32.6 | 43.5 | 26.4 | 27.9 | 25.9 | 32.5 | 33.8 | 33.9 | 22.6 | 22.1 | 24.2 | 14.6 |
| 60% lactose 40% UE 631 | 65% morantel 35% UE 631 | 59.9 | 20.0 | 15.0 | 16.6 | 45.8 | 36.8 | 51.1 | 21.8 | 31.7 | 24.9 | 30.3 | 33.6 | 12.1 | 14.1 | 14.1 | 9.1 | 0.1 |
| 60% lactose 40% UE 631 | 60% morantel 40% UE 631 | 43.2 | 15.45 | 10.3 | 11.0 | 20.3 | 31.6 | 49.3 | 27.1 | 34.5 | 21.8 | 31.2 | 33.9 | 45.2 | 29.1 | 31.5 | 29.2 | 22.7 |
| 100% UE 631 | 60% morantel 40% UE 631 | 34.9 | 12.7 | 4.4 | 5.3 | 17.5 | 16.1 | 22.5 | 26.5 | 18.2 | 10.8 | 16.0 | 14.5 | 14.2 | 6.5 | 12.8 | 13.8 | 10.9 |

EXAMPLE 4

Trial 1 of Devices, in Lambs

Composition, weight and size of devices

These comprised three-layered sanwiches, prepared in the manner of Example 2, containing a centre layer of 60% morantel citrate plus 40% polymer E.V.A grade UE 631.

The outer, thinner layers which are welded to the surfaces of the centre layer, had the following composition in the various devices.

citrate at 10mg/kg on weeks 0, 4 and 8 (days 1, 29 and 57).
Group 3  Rumen device A
Group 4  Rumen device B
Group 5  Rumen device C
Group 6  Rumen device D Given on day 1

The lambs were a Welsh hill cross breed.
On day 1 of dosing the lambs, weighing ca. 25 kg, were about 8 weeks old. These animals were permanently grazed on infected pasture.

No difficulty was encountered with the dosing of the devices using a conventional dosing gun.

(i) Egg counts—Nematodirus

In the untreated control group, counts reached a mean peak level of 291 e.p.g. at week 1, after which they gradually declined to very low levels. From week 9 onwards only 3 of the remaining 6 animals had any counts. In the single treatment control group, counts were reduced to negligible levels for 3 weeks but had started to increase by the fourth week. These increases were much less after the second and third dosings.

In all of the device treated animals, the count fell virtually to zero at week 1 and remained at very low levels for 9 weeks, after which slight increases occurred in most animals.

(ii) Egg counts—Strongyle

In the untreated control group, counts reached a mean peak level of 652 e.p.g. at week 1, after which they dropped to between 200–300 e.p.g. by week 5 and remained near this level for the rest of the experiment.

In the single treatment control group, the first dose virtually eliminated all egg output in all but two animals by week 1, after which a gradual rise occurred by week 4. Similar patterns occurred after treatment at weeks 4 and 8, but the subsequent rise in counts were of a lower magnitude than after the first dosing.

Counts in all of the animals which received devices dropped to low levels after dosing, and with one or two exceptions remained low for the following 12 weeks. counts in animals from groups B and C were consistently lower than those from groups A and D.

(iii) Post-mortem worm counts

Three animals from each group were slaughtered at 4, 8, and 12 weeks after the devices were dosed (week 0). The principal worms present during the experiment were Strongyloides, Trichuris, Ostertagia, Nematodirus and a few Trichostrongylus during the first 8 weeks. Between weeks 8 and 12 numbers of Trichostrongylus increased and Cooperia and Bunostomum appeared. No Haemonchus or Oesophagostomum were present.

The drug was inactive against Strongyloides and Trichuris.

At 4 weeks, low numbers of Ostertagia, Nematodirus, Trichostrongylus and Chabertia were recovered from all the device treated animals. In the group which received a single dose of morantel on week 0, worm numbers were almost as high as those from the untreated controls (i.e. 15,000), although at least 50% were immature forms.

At 8 weeks after dosing, worm numbers from animals given devices A, C and D had increased and of these at least 50% were immatures. Worm numbers remained low in the animals given device B. Worm numbers in the animals with devices were still considerably lower than those recovered from the two control groups.

At 12 weeks, worm numbers recovered from animals with devices had increased substantially but those from device B animals still compared favourably against the control groups. The high number of worms recovered from device groups A, C and D was attributed to the termination of a drug release within the devices between weeks 8 and 12.

Retention of devices in the Rumen

This was satisfactory.

Conclusion

This trial showed that the devices tested gave prolonged effective levels of morantel citrate in the rumen.

EXAMPLE 5

Trial 2 of devices in Lambs

Composition of devices

These were three-layered sandwiches, prepared in the manner of Example 2, containing a centre layer of 60% drug and 40% E.V.A. copolymer (grade UE 631).

The outer layers were welded to the two sides of the centre layer and had the following compositions:

Device A—35% starch+65% E.V.A. (grade EY 902)

Device B—37.5% starch+62.5% E.V.A. (grade EY 902)

Device C—40% starch+60% E.V.A. (grade EY 902)

Device D—As device B, but of reduced size containing 33% lower morantel content.

Size of devices

The overall dimensions unrolled for devices A, B and C were 6.4×6.4×0.18 cm and for device D, 5.3×5.3×0.18 cm. For dosing the devices were rolled into cylinders measuring 6.4×1.3 cm for devices A, B and C, and 5.3×1.2 cm for device D.

Weight of devices

Twenty-four devices were made for each group. Individual weights ranged between 7.3 and 8.4 g for devices A, B, and C, and 5–6 g for devices D, and individual morantel content ranged between about 3.5 and 4 g. for devices A, B and C, and was about 2.5 g for device D.

Animals used

Sixty lambs were used for the anthelmintic test; these were divided into six groups of 12 and treated as follows:

Group 1—Untreated controls
Group 2—Single treatments with morantel citrate at 10 mg/kg on weeks 0, 4 and 7 (days 1, 29 and 50)
Group 3—Rumen device A given on day 1
Group 4—Rumen device B given on day 1
Group 5—Rumen device C given on day 1
Group 6—Rumen device D given on day 1

The lambs were a Suffolk cross breed. On day 1 of dosing the lambs, weighing ca. 40–45 kg, were about 6 months old. No difficulty was encountered with dosing using a conventional dosing gun.

Results

(i) Egg counts—Nematodirus

In the control group, counts in excess of 100 e.p.g. were maintained during the first 7 weeks, after which they gradually declined. Three single doses of morantel at weeks 0, 4 and 7 were very effective in keeping the counts to negligible levels. Low level counts were maintained with:

Device A for 7 weeks
Device B for 6 weeks
Device C for 5 weeks
Device D for 8 weeks
after which increases occurred.

(ii) Egg counts—Strongyle

Those in the control group gradually increased throughout the test from mean levels of 400 e.p.g. to a figure in excess of 2,000 e.p.g. Single treatments of morantel citrate at 10 mg/kg given at weeks 0, 4 and 7 were effective in keeping the counts to low levels throughout the test.

Counts of 400 e.p.g. or less after dosing were maintained with:

Device A for 7 weeks
Device B for 6 weeks
Device C for 5 weeks
Device D for 6 weeks

(iii) Post-mortem worm counts

Good infections of Ostertagia,
T. axei, small intestinal Trichostrongylus, Nematodirus, Cooperia, Bunostomum, Strongyloides, Chabertia and Trichuris were present in the undosed, controls throughout the test.

Worm counts at 4 weeks

Good activity was obtained against all species except Strongyloides and Trichuris in all animals treated with devices.

Retention of devices in the rumen

This was perfectly satisfactory.

Conclusion

Again this trial demonstrated that the devices tested gave prolonged effective levels of morantel citrate in the rumen.

EXAMPLE 6

Devices containing Levamisole

The following devices were prepared in the manner of Example 2:

Device (i)

Inner layer: 40% levamisole HCl in E.V.A. grade UE 631
Outer layers: E.V.A. grade EY 902

Device (ii)

Inner layer: 40% levamisole HCl in E.V.A. grade EY 902
Outer layers: E.V.A. grade EY 902 and were cut into 30×20×1.2 cu.mm. samples for in vitro testing.

EXAMPLE 7

In vitro Test of Example 6 Devices

Test 1

Figure 3:
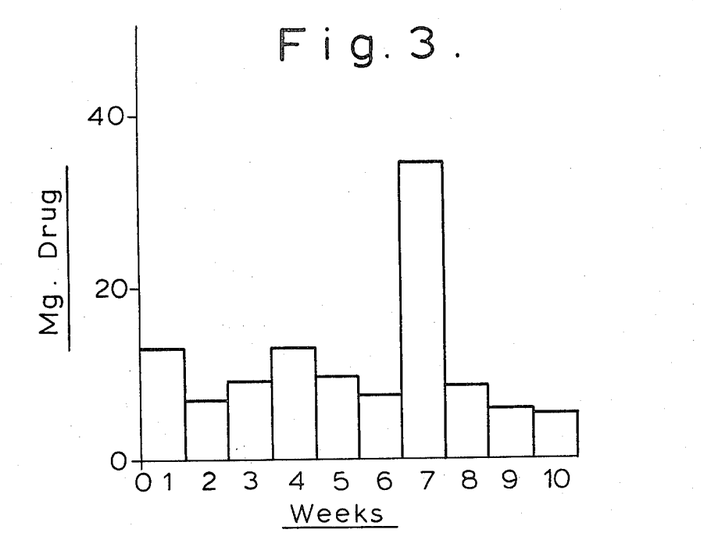
Figure 4:
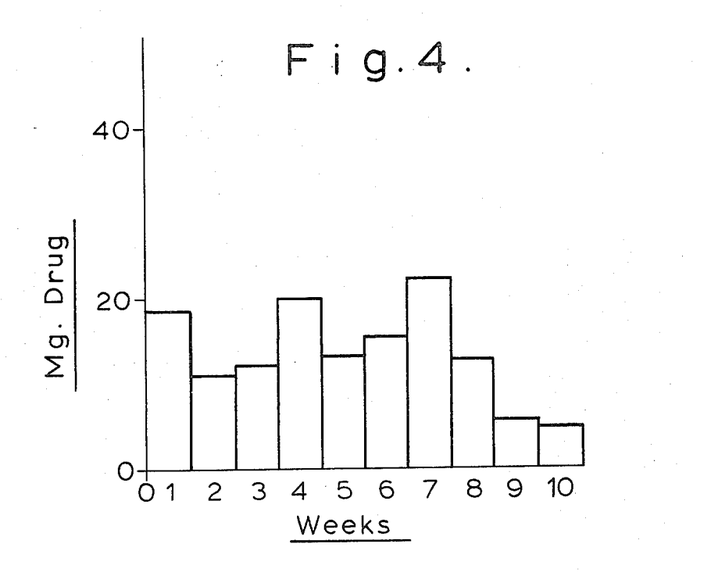

Following the test method of Example 3, but using the Beckmann Spectrophotometer at 213 nm, the results shown in FIGS. 3 and 4 were obtained.

The release rate was fairly constant for the first eight weeks, after which the rate fell.

The softer polymer EY 902 released greater quantities of levamisole than the more rigid UE 631.

Test 2

Figure 5:
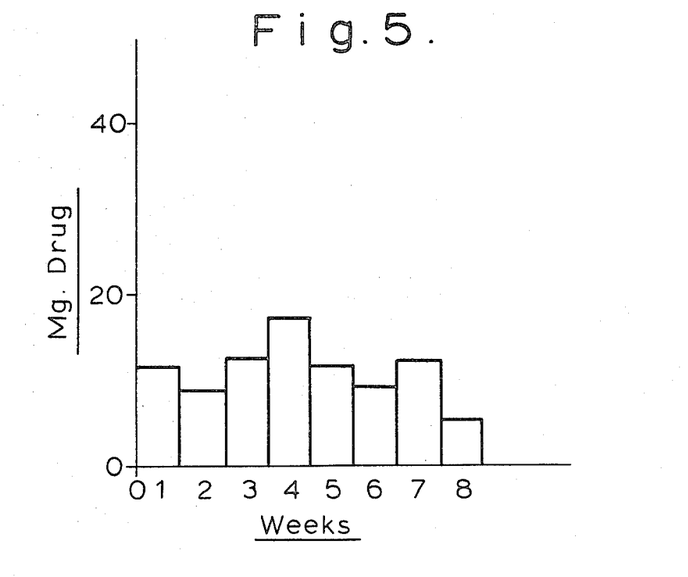
Figure 6:
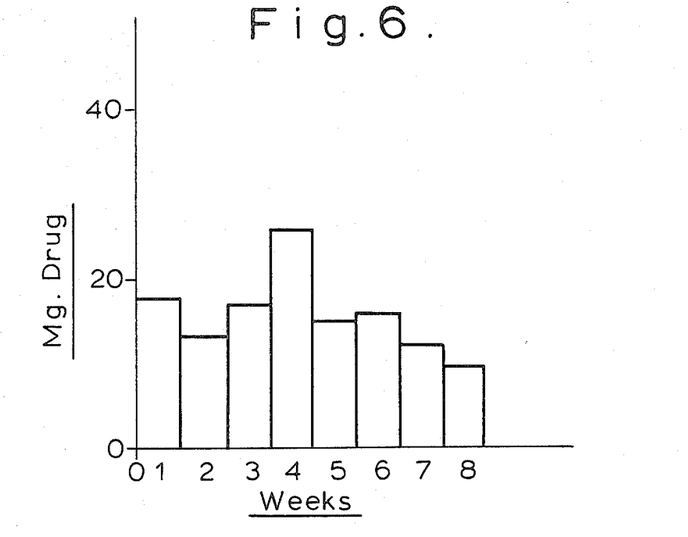

Test 1 was repeated but under more constant temperature control (36° C.). The results obtained are shown in FIGS. 5 and 6.

The results obtained in Test 2 were very similar to those obtained in Test 1.

Conclusion

The ability of the devices to give prolonged levels of levamisole in simulated rumen conditions has been demonstrated.

What we claim is:

1. A device adapted for administration to ruminants comprising a water soluble veterinary medicament dispersed in a resilient sheet of water insoluble ethylene-vinyl acetate copolymer, said medicament being present in an amount corresponding to 30 to 75% by weight of said sheet, said copolymer sheet being of a size and composition such that it is capable of being constrained by constraining means in a rolled-up configuration which permits oral administration, said constraining means being operable to release said constrained sheet in the rumen environment, said sheet when unconstrained thereby assuming an unrolled configuration favoring retention thereof in the rumen.

2. A device according to claim 1 wherein the polymer contains 10 to 60% acetate.

3. A device according to claim 1 wherein the medicant is an anthelmintic.

4. A device according to claim 3 wherein the anthelmintic is morantel, pyrantel, tetramisole, levamisole, butamisole, nitramisole or diethyl cabamazine, a salt thereof, or a salt of nitroxynil.

5. A device according to claim 4 wherein the anthelmintic is morantel, levamisole, or a salt thereof.

6. A device according to claim 1 wherein the medicament is an insecticide, a methane inhibitor, a coccidiostat, a vitamin, a mineral supplement or a growth promotor.

7. A device according to claim 1 wherein the medicament represents 40 to 65% by weight of the sheet.

8. A device according to claim 1 comprising a water soluble anthelmintic dispersed in a sheet of ethylene-vinyl acetate copolymer.

9. A device according to claim 8 wherein the medicament is morantel, levamisole or a salt thereof.

10. A device according to claim 1 wherein said sheet is coated by a film comprising a water-insoluble polymer.

11. A device according to claim 10 wherein the polymer contains 10 to 60% vinyl acetate.

12. A device according to claim 11 wherein the sheet polymer contains from 18 to 21% vinyl acetate.

13. A device according to claim 17 wherein the film polymer contains about 41.7% vinyl acetate.

14. A device according to claim 10 wherein the film contains a water degradable filler.

15. A device according to claim 14 wherein the filler represents 20 to 60% of the film.

16. A device according to claim 15 wherein the filler is starch or lactose.

17. A device according to claim 10 wherein the film covers both surfaces of the sheet.

18. A device according to claim 10 wherein the medicament is an anthelmintic.

19. A device according to claim 18 wherein the anthelmintic is morantel, pyrantel, tetramisole, levamisole, butamisole, nitramisole or diethyl cabamizine, a salt thereof, or a salt of nitroxynil.

20. A device according to claim 18 wherein the anthelmintic represents 40 to 65% by weight of the sheet.

21. A device according to claim 20 wherein the anthelmintic is morantel or a salt thereof.

22. A device according to claim 20 wherein the anthelmintic is levamisole, or a salt thereof.

23. A device according to claim 10 wherein the sheet is an ethylene-vinyl acetate copolymer with a vinyl acetate content of 18 to 21% containing 60% morantel citrate and of thickness 1.0 to 1.5 mm, the film coats both surfaces of the sheet, and said film comprises ethylene-vinyl acetate copolymer and 35 to 40% starch and has a thickness of from 0.2 to 0.4 mm.

24. A method of treatment of disorders in ruminant animals, which method comprises the oral administration to the animal of a device according to claim 1.

* * * * *